(12) United States Patent
Pan

(10) Patent No.: US 10,233,204 B2
(45) Date of Patent: Mar. 19, 2019

(54) PHOSPHAZENE COMPOUND, AND A COMPOSITION, A PREPREG AND A WIRING BOARD COMPRISING THE SAME

(71) Applicant: Guangdong Guangshan New Materials Co., Ltd., Guangdong (CN)

(72) Inventor: Qingchong Pan, Guangdong (CN)

(73) Assignee: GUANGDONG GUANGSHAN NEW MATERIALS CO., LTD., Guangdong (CN)

( * ) Notice: Subject to any disclaimer, the term of this patent is extended or adjusted under 35 U.S.C. 154(b) by 78 days.

(21) Appl. No.: 15/234,014

(22) Filed: Aug. 11, 2016

(65) Prior Publication Data

US 2017/0183366 A1   Jun. 29, 2017

(30) Foreign Application Priority Data

Dec. 29, 2015 (CN) .......................... 2015 1 1025327

(51) Int. Cl.

| | | |
|---|---|---|
| *C07F 9/659* | (2006.01) | |
| *C08J 7/00* | (2006.01) | |
| *C09K 21/12* | (2006.01) | |
| *C07F 9/6593* | (2006.01) | |
| *C08K 5/5399* | (2006.01) | |
| *C08J 5/24* | (2006.01) | |

(52) U.S. Cl.
CPC .......... *C07F 9/659* (2013.01); *C07F 9/65815* (2013.01); *C08J 5/24* (2013.01); *C08K 5/5399* (2013.01); *C09K 21/12* (2013.01); *C08J 2363/04* (2013.01); *C08J 2467/00* (2013.01); *C08J 2479/08* (2013.01); *C08L 2201/02* (2013.01)

(58) Field of Classification Search
CPC ......... C07F 9/65815; C07F 9/659; C08J 5/24; C08J 2363/04; C08J 2467/00; C08J 2479/08; C09K 21/12; C08K 5/5399; C08L 2201/02
USPC ........................................................ 428/413
See application file for complete search history.

(56) References Cited

U.S. PATENT DOCUMENTS

| | | |
|---|---|---|
| 3,891,448 A | 6/1975 | Braxton et al. |
| 4,636,387 A | 1/1987 | Allcock et al. |

FOREIGN PATENT DOCUMENTS

| | | |
|---|---|---|
| CN | 105153234 A | 12/2015 |
| JP | 56-5458 | 1/1981 |
| JP | H04311964 A | 11/1992 |
| JP | H0611877 A | 1/1994 |
| JP | H0635220 A | 2/1994 |
| JP | H0782324 A | 3/1995 |
| JP | 2008164713 | 7/2008 |
| JP | 2008164713 A | 7/2008 |
| JP | 2015205990 A | 11/2015 |

OTHER PUBLICATIONS

Hayata et al., JP 2008-164713 A machine translation in English, Jul. 17, 2008 (Year: 2008).*
Katti et al., "Studies of Phosphazenes Part: 24—Cyclophosphazenecarboxylate Derivatives & Their Use in Synthesis of Amides", Indian Journal of Chemistry, Section A: Inorganic, Physical, Theoretical & Analytical, 1985, vol. 24A, p. 384-386 (Year: 1985).*
Hayes et al., "Copolymerization and Calculation of the Reactivity Ratios for Copoly[methyl methacrylate-methacryloxy penta(trifluoroethoxy)cyclotriphosphazene]", Polymer Preprints, 1994, vol. 35, p. 834-835 (Year: 1994).*
Lanoux et al., "Reactions of the Hydrolyzed Phosphazene N3P3(OCH2CF3)5 ONa", Phosphorus and Sulfur and the Related Elements, 1986, vol. 26, p. 139-142 (Year: 1986).*
European Search Report for Application 16182164.0-1451, dated Nov. 24, 2016, 8 pgs., European Patent Office, Germany.
Singh, S. et al., "Synthesis and Characterization of Amino Acid Substituted Cyclotriphosphazenides." Int. J. Chem. Sci. vol. 9 (2), 2011, pp. 465-469.
"STN Columbus," Columbus, Ohio, US Registry (Online), 2014, pp. 1-16.

* cited by examiner

*Primary Examiner* — David T Karst
(74) *Attorney, Agent, or Firm* — McDonald Hopkins LLC

(57) ABSTRACT

The present invention relates to a phosphazene compound and a composite metal laminate. The phosphazene compound with a partial structure of carboxylic esters has a structure as shown in Formula (I). The present invention obtains a phosphazene compound with a partial structure of carboxylic esters using an M group having specific components. The cured products of the phosphazene compound have good flame retardancy, heat resistance, mechanical properties, flame retardancy, and low dielectric constant, and are a low dielectric flame retardant material having great economic properties and being environmental friendly.

14 Claims, No Drawings

PHOSPHAZENE COMPOUND, AND A COMPOSITION, A PREPREG AND A WIRING BOARD COMPRISING THE SAME

TECHNICAL FIELD

The present invention belongs to the technical field of flame retardant materials, in particular relates to a phosphazene compound with a structure of carboxylic esters, and a composition, a prepreg and a wiring board comprising the same.

BACKGROUND ART

For the purpose of safety, electronic products represented by mobile phones, computers, video cameras and electronic game machines, household and office electrical products represented by air conditioners, refrigerators, television images, audio products etc., and various products used in other areas require different degrees of flame retardancy.

In order to make the products achieve required flame retardant performance or grade, traditional techniques often utilize the following means: adding inorganic flame retardant materials such as types of metal hydroxides comprising crystal water, for example, aluminum hydroxide hydrate, magnesium hydroxide hydrate, and others, into a material system; and adding organic chemicals having a high content of bromine or halogen such as brominated bisphenol A, brominated bisphenol A epoxy resin and others into a material system. In order to improve the flame retardancy of these organic chemicals containing halogen, environmentally unfriendly inorganic chemical flame retardants such as antimony trioxide are often added into the system.

Due to the use of flame retardant materials containing halogen, it can produce toxic substances which cannot degrade or is difficult to degrade such as dioxin type organic halogen chemicals and others when burning, and those toxic substances pollute the environment and affect health of humans and animals.

For the purpose of protecting the environment, the flame retardant effect is achieved by using halogen-free compounds containing phosphorous and/or nitrogen and others as a flame retardant to replace halogen-containing compounds, especially in the electronic, electrical and electronic appliances industries, using reactive mono-functional (which means that there is only one active reactive group in one molecule) 9,10-dihydro-9-oxa-10-phosphaphenanthrene-10-oxide (hereinafter referred to as DOPO simply), more often derivatives of DOPO as a flame retardant component, with or without adding aluminum hydroxide hydrate and magnesium hydroxide hydrate.

In the electronic field, the reaction products (abbreviated as DOPO epoxy resin) of DOPO and high-cost, multifunctional epoxy resin, such as linear phenolic epoxy resin, o-methyl phenolic epoxy resin and bisphenol A phenolic epoxy resin are wisely applied as the epoxy resin material for copper-clad laminate use.

The copper-clad laminates produced by using DOPO epoxy resin have better flame retardancy. However, they have many defects in cohesiveness, heat-resistance and processability, and thus cannot meet the demand of high multilayer, high reliability, high cohesiveness and good processability for manufacturing modern communications. In addition, due to high cost, it is disadvantageous for them to spread to the civilian goods field such as consumer electronics demanding low-cost consumption, for example cell phones.

In the electronic field, DOPO reacts with such as, etherates of bisphenol A, bisphenol F, phenolic resin, phenol and o-cresol, to produce a phenol-containing compound containing DOPO skeleton (collectively called phosphorous-containing phenolic resin) which is used as a curing agent for epoxy resins or an additive for flame retardant materials, and as a flame retardant for epoxy resin materials for copper-clad laminate use.

The copper-clad laminates produced by using phosphorous-containing phenolic aldehyde as a part of or all of the flame retardant ingredients can achieve flame retardancy. However, there are many defects in acid/base resistance, chemical resistance, cohesiveness, heat resistance, processability and so on, so that they cannot meet the demand of high multilayer, high reliability, high cohesiveness and good processability for manufacturing modern communications. In addition, due to high cost, it is disadvantageous for them to spread to the civilian goods field such as consumer electronics demanding low-cost consumption, for example cell phones.

With the factors such as improvement of the electronic industry towards demands of short, small, thin, high multilayer and high reliability, and popularization of civilian consumer electronics, and pressure of more serious environmental pollution, there is an urgent market demand for cheap flame retardant substances having good flame retardancy, heat resistance and good mechanical properties.

CONTENTS OF THE INVENTION

In view of that, on one hand, the present invention provides a phosphazene compound with a structure of carboxylic esters, which has good flame retardancy, heat resistance, mechanical properties, and low dielectric constant and dielectric loss, and moreover has an advantage of being low-cost.

In order to achieve the above purpose, the present invention employs the following technical solution:

A phosphazene compound, having a molecular structure as shown in Formula (I):

Formula (I)

wherein, in Formula (I), $R_1$ represents any organic group; R is an inert nucleophilic group provided by a nucleophile; M is any one of cyclotriphosphazene groups $M_1$, a cyclic ring consisting of four or more phosphazene groups $M_2$, or non-cyclic polyphosphazene groups $M_3$, or a combination of at least two of them;

a is an integer greater than or equal to 0, such as 0, 1, 2, 3, 4, 5, 6, 7; c is an integer greater than or equal to 1, such as 1, 2, 3, 4, 5, 6, 7, with the sum of a and c being greater than or equal to 6. In the present invention, the "a" in $R_a$ means that the number of R group in M group is a. Those skilled in the art can know the connecting relation of these R groups according to the nucleophilic substitution mechanism of halogen substituted phosphazene.

In the present invention, R represents any organic group, with the condition that the atoms thereof do not exceed normal valence state, and can produce a stable compound. "Stable compound" means a compound which can be robustly separated to effective purity from reaction mixture and prepared to an effective compound.

In the present invention, "inert nucleophilic group" means a functional group without an active group, which is difficult to react under common conditions for organic synthesis at an actual speed. It is a remaining functional group after the nucleophilic substitution reaction of nucleophile and chlorinated phosphazene compound, and cannot conduct general reaction.

Preferably, in Formula (I), $R_1$ represents an aliphatic and/or aromatic hydrocarbon group, preferably any one of substituted or unsubstituted straight-chain or branched alkyl, substituted or unsubstituted cycloalkyl, substituted or unsubstituted aralkyl, substituted or unsubstituted alkoxy, substituted or unsubstituted cycloalkoxy, substituted or unsubstituted aralkyloxy, substituted or unsubstituted alkylaryloxy, substituted or unsubstituted aryl or substituted or unsubstituted heteroaryl, or a combination of at least two of them.

Preferably, $R_1$ is any one of unsubstituted straight-chain or branched alkyl, unsubstituted cycloalkyl, unsubstituted aralkyl, unsubstituted alkoxy, unsubstituted cycloalkoxy, unsubstituted aralkyloxy, unsubstituted alkylaryloxy, unsubstituted aryl or unsubstituted heteroaryl, or a combination of at least two of them.

Preferably, $R_1$ does not contain a reactive group which can react with epoxy resin to produce a secondary hydroxyl.

In the present invention, when "a" is not zero, it means the phosphazene is substituted by the R group. In the present invention, nucleophile means those which can conduct nucleophilic substitution reaction with halogenated phosphazene. During the nucleophilic substitution reaction, nucleophile removes leaving groups, nucleophilic groups attack halogen atoms in halogenated phosphazene, and nucleophilic groups are attached to M. For example, when employing methanol $CH_3OH$ as a nucleophile to conduct nucleophilic substitution reaction with halogenated phosphazene, $CH_3OH$ removes $H^+$, methoxyl $CH_3O-$ substitutes the halogen atom in halogenated phosphazene and is attached to $-P$ in phosphazene, and in this case, R is $CH_3O-$.

Preferably, the inert nucleophilic group has a structure of Y—X—, wherein, X preferably is O, C, N; Y is an aliphatic and/or aromatic hydrocarbon group, further preferably any one of substituted or unsubstituted straight-chain or branched alkyl, substituted or unsubstituted cycloalkyl, substituted or unsubstituted aralkyl, substituted or unsubstituted alkoxy, substituted or unsubstituted cycloalkoxy, substituted or unsubstituted aralkyloxy, substituted or unsubstituted alkylaryloxy, substituted or unsubstituted aryl or substituted or unsubstituted heteroaryl, or a combination of at least two of them.

Further preferably, the inert nucleophilic group R is selected from any one of $-OR_{13}$, $-SR_{14}$,

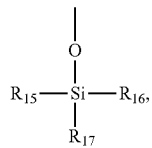

$-C\equiv C-R_{18}$, $R_{22}-COO-$,

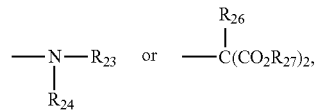

or a combination of at least two of them.

$R_{13}$ is any one of substituted or unsubstituted straight-chain or branched alkyl, substituted or unsubstituted cycloalkyl, substituted or unsubstituted aralkyl, substituted or unsubstituted alkoxy, substituted or unsubstituted cycloalkoxy, substituted or unsubstituted aralkyloxy, substituted or unsubstituted alkylaryloxy, substituted or unsubstituted carbonate group, substituted or unsubstituted sulfonate group, substituted or unsubstituted phosphonate group, substituted or unsubstituted aryl or substituted or unsubstituted heteroaryl, or a combination of at least two of them. $R_{14}$ is any one of substituted or unsubstituted straight-chain or branched alkyl, substituted or unsubstituted cycloalkyl, substituted or unsubstituted aralkyl, substituted or unsubstituted alkoxy, substituted or unsubstituted cycloalkoxy, substituted or unsubstituted aralkyloxy, substituted or unsubstituted alkylaryloxy, substituted or unsubstituted aryl or substituted or unsubstituted heteroaryl, or a combination of at least two of them. $R_{15}$, $R_{16}$ and $R_{17}$ are independently any one of substituted or unsubstituted straight-chain or branched alkyl, substituted or unsubstituted cycloalkyl, substituted or unsubstituted aralkyl, substituted or unsubstituted alkoxy, substituted or unsubstituted cycloalkoxy, substituted or unsubstituted aralkyloxy, substituted or unsubstituted alkylaryloxy, substituted or unsubstituted aryl or substituted or unsubstituted heteroaryl. $R_{18}$ is any one of substituted or unsubstituted straight-chain or branched alkyl, substituted or unsubstituted cycloalkyl, substituted or unsubstituted aralkyl, substituted or unsubstituted alkoxy, substituted or unsubstituted cycloalkoxy, substituted or unsubstituted aralkyloxy, substituted or unsubstituted alkylaryloxy, substituted or unsubstituted aryl or substituted or unsubstituted heteroaryl, or a combination of at least two of them. $R_{22}$ is any one of substituted or unsubstituted straight-chain or branched alkyl, substituted or unsubstituted cycloalkyl, substituted or unsubstituted aralkyl, substituted or unsubstituted alkoxy, substituted or unsubstituted cycloalkoxy, substituted or unsubstituted aralkyloxy, substituted or unsubstituted alkylaryloxy, substituted or unsubstituted aryl or substituted or unsubstituted heteroaryl, or a combination of at least two of them. $R_{23}$ and $R_{24}$ are independently any one of substituted or unsubstituted straight-chain or branched alkyl, substituted or unsubstituted cycloalkyl, substituted or unsubstituted aralkyl, substituted or unsubstituted alkoxy, substituted or unsubstituted cycloalkoxy, substituted or unsubstituted aralkyloxy, substituted or unsubstituted alkylaryloxy, substituted or unsubstituted aryl or substituted or unsubstituted heteroaryl, or a combination of at least two of them. $R_{26}$ and $R_{27}$ are independently any one of substituted or unsubstituted straight-chain or branched alkyl, substituted or unsubstituted cycloalkyl, substituted or unsubstituted aralkyl, substituted or unsubstituted alkoxy, substituted or unsubstituted cycloalkoxy, substituted or unsubstituted aralkyloxy, substituted or unsubstituted alkylaryloxy, substituted or unsubstituted aryl or substituted or unsubstituted heteroaryl, or a combination of at least two of them.

In the previous text, the substituted or unsubstituted straight-chain or branched alkyl is preferably substituted or unsubstituted C1-C12 (for example, C1, C2, C3, C4, C5, C6, C7, C8, C9, C10 or C11) straight-chain or branched alkyl, preferably C1-C8 straight-chain or branched alkyl. When the number of carbon atom is 1, it is methyl; when the number of carbon atom is 2, it is ethyl.

The substituted or unsubstituted cycloalkyl is preferably C3-C12 (for example, C4, C5, C6, C7, C8, C9, C10 or C11) substituted or unsubstituted cycloalkyl.

The substituted or unsubstituted aryl is preferably phenyl, benzyl, 1,2,3,4-tetrahydronaphthyl,

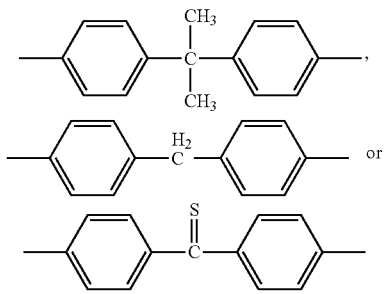

etc. The examples of phenyl are biphenylyl, terphenylyl, phenylmethyl, phenylethyl, and phenylpropyl, etc.

The unsubstituted aryl or substituted or unsubstituted heteroaryl is five-membered or six-membered heteroaryl.

The substituted or unsubstituted alkoxy is C1-C12 (for example, C1, C2, C3, C4, C5, C6, C7, C8, C9, C10 or C11) alkoxy.

The substituted or unsubstituted aralkyl is C7-C12 (for example, C8, C9, C10 or C11) aralkyl.

The substituted or unsubstituted cycloalkoxy is C3-C8 (for example, C4, C5, C6, C7 or C8) cycloalkoxy.

The substituted or unsubstituted aralkyloxy is C7-C12 (for example, C8, C9, C10 or C11) aralkyloxy.

The substituted or unsubstituted alkylaryloxy is C7-C12 (for example, C8, C9, C10 or C11) alkylaryloxy.

Preferably, R is substituted or unsubstituted alkoxy or aryloxy.

The examples of alkoxy include, but not limited to, methoxy, ethoxy, isopropoxy, propoxy, butoxy and pentoxy. The alkoxy group can be substituted by the following substituents: alkenyl, alkynyl, halogen, hydroxyl, alkyl carbonyloxy, arylcarbonyloxy, alkoxycarbonyl oxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiolcarbonyl, alkoxy, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, mercapto, thiocarboxylate, sulphate, alkylsulfinyl, sulfonic acid group, sulfamoyl, sulfonamido, nitromethyl, trifluoromethyl, cyano, azido, heterocyclic group, alkylaryl or aromatic or heteroaromatic group. The examples of the alkoxy group substituted by halogen include, but not limited to, monofluoromethoxy group, difluoromethoxy group, trifluoromethoxy group, monochloromethoxy group, dichloromethoxy group, trichloromethoxy group.

The examples of aryloxy include phenoxy, benzyloxy, naphthyloxy or biphenyloxy. The aryloxy can be substituted by alkyl.

preferably, the phosphazene compound is any one of the phosphazene compounds having the following structures or a mixture of at least two of them:

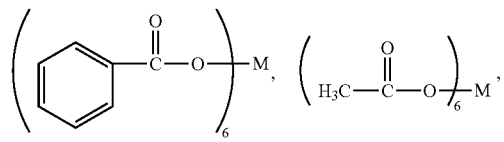

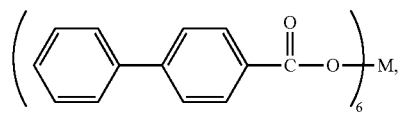

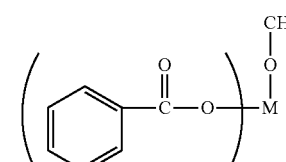

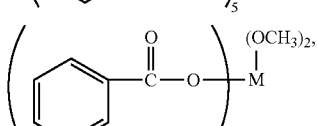

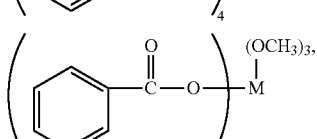

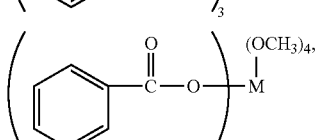

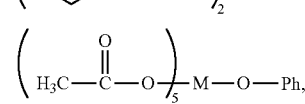

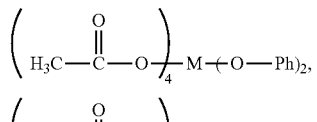

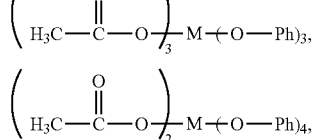

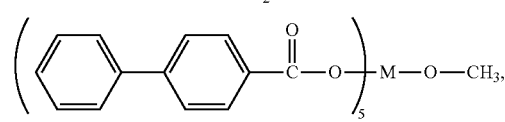

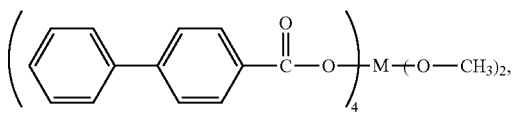

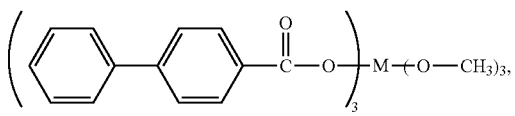

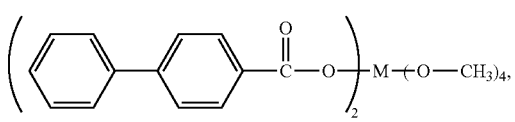

-continued $$\left(\bigotimes\!\!-COO\right)_6 M,$$

$$\left(\bigotimes\!\!-COO\right)_5 M\!-\!O\!-\!\bigcirc,$$

$$\left(\bigotimes\!\!-COO\right)_4 M\!\left(\!O\!-\!\bigcirc\right)_2,$$

$$\left(\bigotimes\!\!-COO\right)_3 M\!\left(\!O\!-\!\bigcirc\right)_3,$$

$$\left(\bigotimes\!\!-COO\right)_2 M\!\left(\!O\!-\!\bigcirc\right)_4,$$

$$\left(\bigotimes\!\!-COO\right)_5 M\!-\!O\!-\!CH_3,$$

$$\left(\bigotimes\!\!-COO\right)_4 M\!-\!(O\!-\!CH_3)_2,$$

$$\left(\bigotimes\!\!-COO\right)_3 M\!-\!(O\!-\!CH_3)_3 \text{ or}$$

$$\left(\bigotimes\!\!-COO\right)_2 M\!-\!(O\!-\!CH_3)_4.$$

In the present invention, preferably, the structure of $M_1$ is:

$$\left[\!\!\begin{array}{c}\diagdown\!\!\diagup\\P\!=\!N\end{array}\!\!\right]_3;$$

the structure of $M_2$ is:

$$\left[\!\!\begin{array}{c}\diagdown\!\!\diagup\\P\!=\!N\end{array}\!\!\right]_x;$$

wherein, x is greater than or equal to 4;
the structure of $M_3$ is:

$$*\!-\!\!\left[\!\!\begin{array}{c}\diagdown\!\!\diagup\\P\!=\!N\end{array}\!\!\right]_y\!-\!*,$$

wherein, y is greater than or equal to 3.

It should be noted that, in the expression for structures of $M_1$ and $M_2$, the symbol of $$`` \bigcup ''$$

is merely a schematic illustration for cyclic structure; in the structure $$`` \!-\!\!\begin{array}{c}\diagdown\!\!\diagup\\P\!=\!N\end{array}\!-\!\!''$$

of the structural formulas of $M_1$, $M_2$ and $M_3$, the bonds connected to the P atom only represent that the substitutions of substituents take place on the P atom, and should not be construed as methyl.

In another aspect, the present invention provides a method for preparing a phosphazene compound with a structure of carboxylic esters. The phosphazene compound prepared by this method has good flame retardancy, heat resistance, good mechanical properties, and low dielectric constant.

A method for preparing the above phosphazene compound, by carrying out a nucleophilic substitution reaction of phosphazene chloride and nucleophile.

The nucleophile is a monofunctional acid.

In the nucleophilic substitution reaction, chlorine atom is substituted by —$COOR_1$, and a chlorizated salt is obtained. The nucleophilic substitution reaction can be carried out by methods well-known in the art. Specific examples of catalysts are metal chlorides such as zinc chloride, magnesium chloride, aluminum chloride; boron trifluoride and complexes thereof; Lewis bases such as sodium hydroxide. These catalysts may be used alone or in combination, which is not specifically defined in the present invention. Hexachlorocyclotriphosphazene of which the source is the most extensive and others can be used as phosphazene chloride. In order to obtain the R group in the target product, a nucleophile which can provide R groups can be added at the same time. For example, when R is alkoxy or phenoxy, methanol or phenol can be added to carry out mix substitution, i.e. chlorine atoms are substituted by R and —$COOR_1$ simultaneously. Of course, partial chlorine atoms of hexachlorocyclotriphosphazene can be substituted by using a nucleophile which can provide R groups prior to reacting with a nucleophile.

In the present invention, the phosphazene compound does not contain halogen.

Preferably, the preparation method is that the phosphazene chloride first reacts with R—Na, and then reacts with $R_1COOH$ to obtain the phosphazene compound. Wherein, R and $R_1$ have the same meaning as the previously mentioned R and $R_1$.

In another aspect, the present invention provides an epoxy resin composition having good flame retardancy, heat resistance, good mechanical properties, and low dielectric constant.

The above phosphazene compound with a structure of carboxylic esters is added into the epoxy resin composition as a flame retardant.

Epoxy resin, curing agent, other fillers of the epoxy resin composition can utilize well-known epoxy resins, curing agents and fillers in the art.

The epoxy resin composition can also contain other polyesters in addition to the polyesters comprising phosphazene structure.

The epoxy resin composition can be made into a prepreg according to actual needs.

A prepreg prepared by impregnating a substrate with the above epoxy resin composition or coating the above epoxy resin composition onto a substrate.

The substrate can be a glass fiber substrate, a polyester substrate, a polyimide substrate, a ceramic substrate or a carbon fiber substrate, etc.

Here, the specific process conditions of impregnation or coating are not particularly limited. The "prepreg" is a "bonding sheet" well-known by those skilled in the art.

A composite metal laminate comprising more than one sheet of the prepregs described above and prepared by coating metal layer on the surface of the prepregs, overlapping and pressing successively.

Here, the material of the surface-coated metal layer is aluminum, copper, iron and alloys of any combination thereof.

Specific examples of the composite metal laminate are CEM-1 copper clad laminate, CEM-3 copper clad laminate, FR-4 copper clad laminate, FR-5 copper clad laminate, CEM-1 aluminum clad laminate, CEM-3 aluminum clad laminate, FR-4 aluminum clad laminate, FR-5 aluminum clad laminate.

A wiring board prepared by processing wires on the surface of the composite metal laminate as described above.

The raw materials of the epoxy resin composition form a coating having good flame retardancy on the composite metal laminate by curing, and this can improve the wide use of the wiring board in industries of machine, equipment, instrument, meter, etc. which need a wiring board, for example electronic industry, electrical and electrical appliance industry, transportation industry, aerospace industry, toy industry, etc.

The above term "xxxyl or group" refers to the remaining parts of the molecular structure of corresponding compounds after one or more hydrogen atoms or other atoms or atomic groups are removed.

The present invention obtains a flame retardant compound using an M group having specific components. The M group makes the flame retardant compound have good flame retardancy. The cured products of the flame retardant compound have good flame retardancy, heat resistance, mechanical properties, and low dielectric constant and dielectric loss, and are a low dielectric flame retardant material also having great economic properties and being environmental friendly.

EMBODIMENTS

The technical solution of the present invention is further described by the following examples.

Example 1

The phosphazene compound of the present example has the following structure:

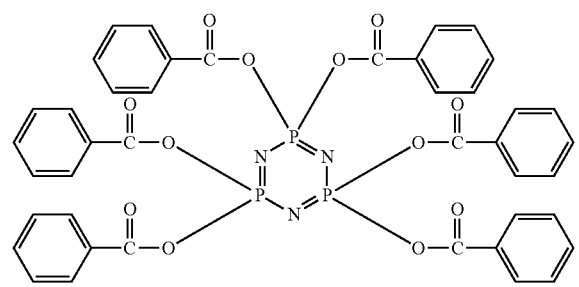 [SMILES: O=C(OP1(OC(=O)c2ccccc2)=NP(OC(=O)c2ccccc2)(OC(=O)c2ccccc2)=NP(OC(=O)c2ccccc2)(OC(=O)c2ccccc2)=N1)c1ccccc1]

1 mol of hexachlorocyclotriphosphazene, 200 ml of acetone, 6 mol of benzoic acid were added to a 3-neck glass reactor having a volume of 2000 ml and having a stirring apparatus. While stirring, nitrogen was fed therein, and the reactor was heated to 60° C. 620 g of 20% sodium hydroxide solution was dripped within 60 min, and then the mixture was held at 60° C., stirred and reacted for 15 hours. After reaction, the salts and water in the system were removed by physical method; the insoluble substance in the system was removed by filtration; and the solvent in the system was distilled to obtain a low dielectric flame retardant compound. The flame retardant compound was measured to have an ester equivalent of 150 g/eq, and such target compound was named as compound A.

150 g (1 eq) of the above A product, 200 g (1 eq) of o-cresol novolac epoxy resin with an epoxy equivalent of 200 g/eq and 0.2 g of pyridine were dissolved into solution using an appropriate amount of butanone. A copper clad laminate a with a resin content of 50% is prepared by using standard glass cloths according to a generally used production process. The properties of copper clad laminate a are shown in Table 1.

The obtained compound A was characterized by nuclear magnetic resonance hydrogen spectrum, and the results are as follows:

$^1$H NMR (CDCl$_3$, 500 MHz): ☐8.13, (s, 12H, hydrogen at an ortho-position to ester group in phenyl), 7.47 (m, 12H, hydrogen at a meta-position to ester group in phenyl), 7.60 (m, 6H, hydrogen at a para-position to ester group in phenyl).

Characteristic peak positions in infrared spectroscopy: ester carbonyl, 1730-1740 cm$^{-1}$; C—O—C in ester group, 1200 cm$^{-1}$.

Example 2

The phosphazene compound of the present example has the following structure:

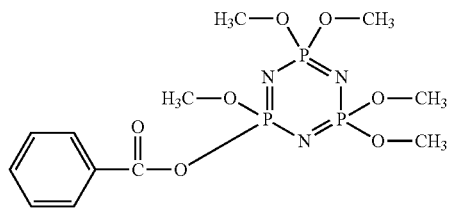 [SMILES: COP1(OC)=NP(OC)(OC)=NP(OC)(OC(=O)c2ccccc2)=N1]

1 mol of hexachlorocyclotriphosphazene, 200 ml of acetone, 3 mol of benzoic acid and 3 mol of sodium methoxide were added to a 3-neck glass reactor having a volume of 2000 ml and having a stirring apparatus. While stirring, nitrogen was fed therein, and the reactor was heated to 60° C. 620 g of 20% sodium hydroxide solution was dripped within 60 min, and then the mixture was held at 60° C., stirred and reacted for 15 hours. After reaction, the salts and water in the system were removed by physical method; the insoluble substance in the system was removed by filtration; and the solvent in the system was distilled to obtain 1 mol of a flame retardant compound. The flame retardant compound was measured to have an ester equivalent of 80 g/eq, and such target compound was named as compound B.

$^1$H NMR (CDCl$_3$, 500 MHz): □ 3.39 (m, 15H, hydrogen in methyl), 8.13, (s, 12H, hydrogen at an ortho-position to ester group in phenyl), 7.47 (m, 12H, hydrogen at a meta-position to ester group in phenyl), 7.60 (m, 6H, hydrogen at a para-position to ester group in phenyl).

Characteristic peak positions in infrared spectroscopy: ester carbonyl, 1730-1740 cm$^{-1}$; C—O—C in ester group, 1200 cm$^{-1}$.

100 g of o-cresol novolac epoxy resin with an epoxy equivalent of 200 g/eq and 0.2 g of pyridine were added into 1125 g of the above B product and the mixture was dissolved into solution using an appropriate amount of butanone. A copper clad laminate b with a resin content of 50% is prepared by using standard glass cloths according to a generally used production process. The properties of copper clad laminate b are shown in Table 1.

Example 3

200 g of bisphenol-A novolac epoxy resin with an epoxy equivalent of 200 g/eq and 0.2 g of pyridine were added into 75 g of the above A product and 110 g of an ester compound with an ester equivalent of 220 g/eq as shown in the following formula (a product of Guangdong Guangshan New Materials Co., Ltd, YEH-6611), and the mixture was dissolved into solution using an appropriate amount of butanone. A copper clad laminate c with a resin content of 50% is prepared by using standard glass cloths according to a generally used production process. The properties of copper clad laminate c are shown in Table 1.

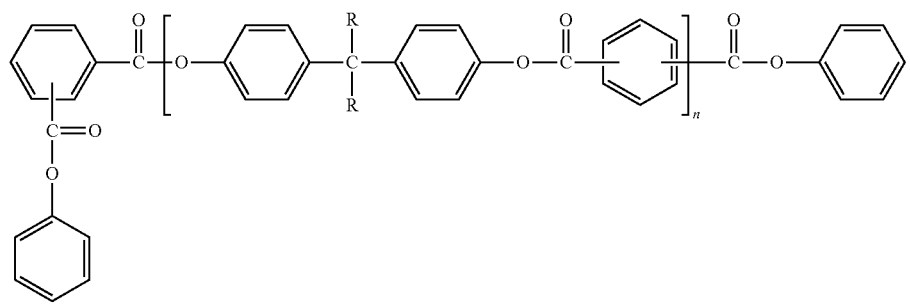

Comparative Example 1

105 g linear phenolic resin curing agent with a phenolic hydroxyl group equivalent of 105 g/eq, 70 g of hexaphenoxyphosphacyanogen used as a flame retardant and 0.2 g of 2-methylimidazole were added into 200 g of o-methyl phenolic epoxy resin with an epoxy equivalent of 200 g/eq, and the mixture was dissolved into solution using an appropriate amount of butanone. A copper clad laminate d with a resin content of 50% is prepared by using standard glass cloths according to a generally used production process. The properties of copper clad laminate d are shown in Table 1.

Comparative Example 2

70 g of hexaphenoxyphosphacyanogen used as a flame retardant, 220 g of YEH-6611 and 0.2 g of pyridine were added into 200 g of o-methyl phenolic epoxy resin with an epoxy equivalent of 200 g/eq, and the mixture was dissolved into solution using an appropriate amount of butanone. A copper clad laminate e with a resin content of 50% is prepared by using standard glass cloths according to a generally used production process. The properties of copper clad laminate e are shown in Table 1.

The test results of products of Examples and Comparative Examples are shown in Table 1 (the specific test methods are not described considering that they are well-known by those skilled in the art).

TABLE 1

Comparison of properties of each copper clad laminate

| Test Item | copper clad laminate a | copper clad laminate b | copper clad laminate c | copper clad laminate d | copper clad laminate e |
|---|---|---|---|---|---|
| combustibility (UL-90) | V0 | V0 | V0 | V0 | V0 |
| Dielectric constant (5 MHz) | 3.2 | 3.3 | 3.4 | 4.5 | 4.6 |
| Dielectric loss (5 MHz) | 0.004 | 0.004 | 0.005 | 0.015 | 0.018 |
| water absorption (%) | 0.32 | 0.31 | 0.38 | 0.52 | 0.58 |
| Tg(° C.) | 178 | 173 | 170 | 148 | 150 |
| Peeling strength (N · mm$^{-1}$) | 2.21 | 2.03 | 2.02 | 2.02 | 2.02 |

The present invention describes the detailed technological equipment and process by the aforesaid examples, but the present invention is not limited by the aforesaid detailed technological equipment and process. That is to say, it does not mean that the present invention cannot be fulfilled unless relying on the aforesaid detailed technological equipment and process. Those skilled in the art shall know that, any modification to the present invention, any equivalent replacement of each raw material of the product of the present invention and the addition of auxiliary ingredient, the selection of specific embodiment and the like all fall into the protection scope and the disclosure scope of the present invention.

The invention claimed is:

1. A phosphazene compound, characterized in that, it has a molecular structure as shown in Formula (I):

Formula (I)

$(R)_a$—M—$(OOCR_1)_c$;

in Formula (I), $R_1$ represents any organic group; R is an inert nucleophilic group provided by a nucleophile; M is any one of cyclotriphosphazene groups $M_1$, cyclic ring consisting of four or more phosphazene groups $M_2$, or non-cyclic polyphosphazene groups $M_3$, or a combination of at least two of them;

a is an integer of 1-4; c is an integer greater than or equal to 1, with the sum of a and c being greater than or equal to 6.

2. The phosphazene compound of claim 1, characterized in that, $R_1$ is an aliphatic and/or aromatic hydrocarbon group.

3. The phosphazene compound of claim 2, characterized in that, $R_1$ is any one of substituted or unsubstituted straight-chain or branched alkyl, substituted or unsubstituted cycloalkyl, substituted or unsubstituted aralkyl, substituted or unsubstituted alkoxy, substituted or unsubstituted cycloalkoxy, substituted or unsubstituted aralkyloxy, substituted or unsubstituted alkylaryloxy, substituted or unsubstituted aryl or substituted or unsubstituted heteroaryl, or a combination of at least two of them.

4. The phosphazene compound of claim 3, characterized in that, $R_1$ is any one of unsubstituted straight-chain or branched alkyl, unsubstituted cycloalkyl, unsubstituted aralkyl, unsubstituted alkoxy, unsubstituted cycloalkoxy, unsubstituted aralkyloxy, unsubstituted alkylaryloxy, unsubstituted aryl or unsubstituted heteroaryl, or a combination of at least two of them.

5. The phosphazene compound of claim 1, characterized in that, $R_1$ does not contain a reactive group which can react with epoxy resin to produce a secondary hydroxyl.

6. The phosphazene compound of claim 1, characterized in that, the inert nucleophilic group R has a structure of Y—X—; X is O, C, N; Y is an aliphatic and/or aromatic hydrocarbon group.

7. The phosphazene compound of claim 6, characterized in that, Y is any one of substituted or unsubstituted straight-chain or branched alkyl, substituted or unsubstituted cycloalkyl, substituted or unsubstituted aralkyl, substituted or unsubstituted alkoxy, substituted or unsubstituted cycloalkoxy, substituted or unsubstituted aralkyloxy, substituted or unsubstituted alkylaryloxy, substituted or unsubstituted aryl or substituted or unsubstituted heteroaryl, or a combination of at least two of them.

8. The phosphazene compound of claim 1, characterized in that, R is any one selected from the group consisting of —$OR_{13}$,

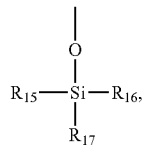

—C≡C—$R_{18}$, $R_{22}$—COO—,

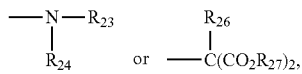

or a combination of at least two of them;

$R_{13}$ is any one of substituted or unsubstituted straight-chain or branched alkyl, substituted or unsubstituted cycloalkyl, substituted or unsubstituted aralkyl, substituted or unsubstituted alkoxy, substituted or unsubstituted cycloalkoxy, substituted or unsubstituted aralkyloxy, substituted or unsubstituted alkylaryloxy, substituted or unsubstituted carbonate group, substituted or unsubstituted sulfonate group, substituted or unsubstituted phosphonate group, substituted or unsubstituted aryl or substituted or unsubstituted heteroaryl, or a combination of at least two of them; $R_{14}$ is any one of substituted or unsubstituted straight-chain or branched alkyl, substituted or unsubstituted cycloalkyl, substituted or unsubstituted aralkyl, substituted or unsubstituted alkoxy, substituted or unsubstituted cycloalkoxy, substituted or unsubstituted aralkyloxy, substituted or unsubstituted alkylaryloxy, substituted or unsubstituted aryl or substituted or unsubstituted heteroaryl, or a combination of at least two of them; $R_{15}$, $R_{16}$ and $R_{17}$ are independently any one of substituted or unsubstituted straight-chain or branched alkyl, substituted or unsubstituted cycloalkyl, substituted or unsubstituted aralkyl, substituted or unsubstituted alkoxy, substituted or unsubstituted cycloalkoxy, substituted or unsubstituted aralkyloxy, substituted or unsubstituted alkylaryloxy, substituted or unsubstituted aryl or substituted or unsubstituted heteroaryl, or a combination of at least two of them; $R_{18}$ is any one of substituted or unsubstituted straight-chain or branched alkyl, substituted or unsubstituted cycloalkyl, substituted or unsubstituted aralkyl, substituted or unsubstituted alkoxy, substituted or unsubstituted cycloalkoxy, substituted or unsubstituted aralkyloxy, substituted or unsubstituted alkylaryloxy, substituted or unsubstituted aryl or substituted or unsubstituted heteroaryl, or a combination of at least two of them; $R_{22}$ is any one of substituted or unsubstituted straight-chain or branched alkyl, substituted or unsubstituted cycloalkyl, substituted or unsubstituted aralkyl, substituted or unsubstituted alkoxy, substituted or unsubstituted cycloalkoxy, substituted or unsubstituted aralkyloxy, substituted or unsubstituted alkylaryloxy, substituted or unsubstituted aryl or substituted or unsubstituted heteroaryl, or a combination of at least two of them; $R_{23}$ and $R_{24}$ are independently any one of substituted or unsubstituted straight-chain or branched alkyl, substituted or unsubstituted cycloalkyl, substituted or unsubstituted aralkyl, substituted or unsubstituted alkoxy, substituted or unsubstituted cycloalkoxy, substituted or unsubstituted aralkyloxy, substituted or unsubstituted alkylaryloxy, substituted or unsubstituted aryl or substituted or unsubstituted heteroaryl, or a combination of at least two of them; $R_{26}$ and $R_{27}$ are independently any one of substituted or unsubstituted straight-chain or branched alkyl, substituted or unsubstituted cycloalkyl, substituted or unsubstituted aralkyl, substituted or unsubstituted alkoxy, substituted or unsubstituted cycloalkoxy, substituted or unsubstituted aralkyloxy, substituted or unsubstituted alkylaryloxy, substituted or unsubstituted aryl or substituted or unsubstituted heteroaryl, or a combination of at least two of them.

9. The phosphazene compound of claim 1, characterized in that, the phosphazene compound is any one of the phosphazene compounds having the following structures or a mixture of at least two of them:

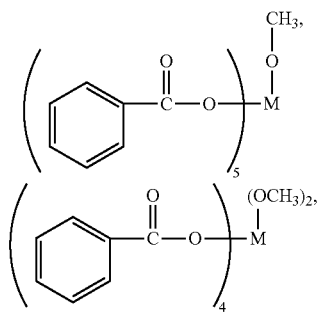

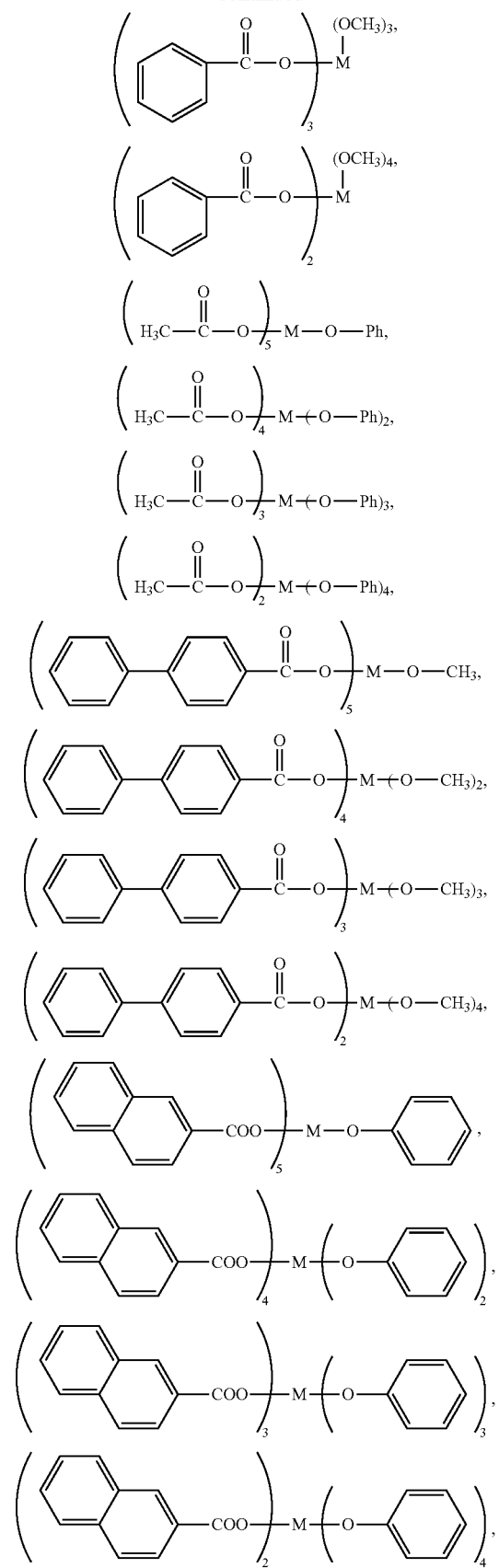

-continued

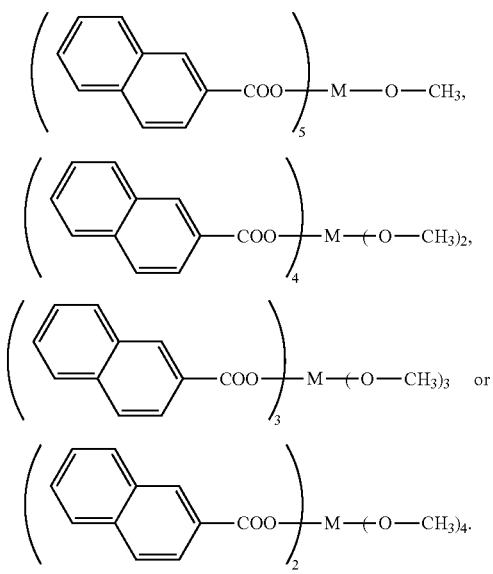

10. The phosphazene compound of claim 1, characterized in that, the structure of $M_1$ is:

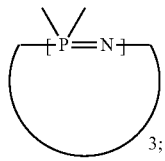

the structure of $M_2$ is:

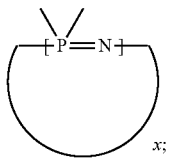

wherein, x is greater than or equal to 4;
the structure of $M_3$ is:

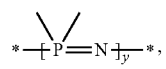

wherein, y is greater than or equal to 3.

11. A method for preparing the phosphazene compound of claim 1, characterized in that, the phosphazene compound is obtained by carrying out a nucleophilic substitution reaction of phosphazene chloride and nucleophile.

12. The method of claim 11, characterized in that, the preparation method is that the phosphazene chloride firstly reacts with R—Na, and then reacts with $R_1COOH$ to obtain the phosphazene compound of claim 1.

13. A prepreg, characterized in that, it is prepared by impregnating a substrate with an epoxy resin composition comprising the phosphazene compound of claim 1 or coating an epoxy resin composition comprising the phosphazene compound of claim 1 onto a substrate.

14. The prepreg of claim 13, characterized in that, the substrate is a glass fiber substrate, a polyester substrate, a polyimide substrate, a ceramic substrate or a carbon fiber substrate.

* * * * *